(12) United States Patent
Smith et al.

(10) Patent No.: US 8,419,743 B2
(45) Date of Patent: *Apr. 16, 2013

(54) ASSEMBLY TOOL FOR MODULAR IMPLANTS AND ASSOCIATED METHOD

(75) Inventors: Aaron P. Smith, Warsaw, IN (US); Tyler D. Witt, Fond du Lac, WI (US); Andrew Freiberg, Weston, MA (US)

(73) Assignee: Biomet Manufacturing Corp., Warsaw, IN (US)

(*) Notice: Subject to any disclaimer, the term of this patent is extended or adjusted under 35 U.S.C. 154(b) by 317 days.

This patent is subject to a terminal disclaimer.

(21) Appl. No.: 12/718,027

(22) Filed: Mar. 5, 2010

(65) Prior Publication Data

US 2011/0218583 A1   Sep. 8, 2011

(51) Int. Cl.
- A61B 17/58 (2006.01)
- A61B 17/60 (2006.01)
- A61F 2/00 (2006.01)
- A61F 2/42 (2006.01)

(52) U.S. Cl.
USPC ................................ 606/99; 623/22.12

(58) Field of Classification Search .............. 606/99; 623/22.12
See application file for complete search history.

(56) References Cited

U.S. PATENT DOCUMENTS

| | | |
|---|---|---|
| 2,231,864 A | 2/1941 | Abel |
| 3,815,599 A | 6/1974 | Deyerle |
| 4,306,550 A | 12/1981 | Forte |
| 4,549,319 A | 10/1985 | Meyer |
| 4,552,136 A | 11/1985 | Kenna |
| 4,601,289 A | 7/1986 | Chiarizzio et al. |
| 4,718,915 A | 1/1988 | Epinette |
| 4,728,333 A | 3/1988 | Masse et al. |
| 4,790,852 A | 12/1988 | Noiles |
| 4,842,606 A | 6/1989 | Kranz et al. |
| 4,883,492 A | 11/1989 | Frey et al. |
| 4,904,269 A | 2/1990 | Elloy et al. |
| 4,959,066 A | 9/1990 | Dunn et al. |
| 5,041,118 A | 8/1991 | Wasilewski |
| 5,047,035 A | 9/1991 | Mikhail et al. |
| 5,061,271 A | 10/1991 | Van Zile |
| 5,089,004 A | 2/1992 | Averill et al. |

(Continued)

FOREIGN PATENT DOCUMENTS

| | | |
|---|---|---|
| DE | 29516473 U1 | 12/1995 |
| EP | 0453695 A1 | 10/1991 |

(Continued)

OTHER PUBLICATIONS

DePuy, a Johnson & Johnson company, "REEF: Distally Interlocked Modular Femoral Reconstruction Prosthesis", 2004, 7 sheets.

(Continued)

*Primary Examiner* — Kevin T Truong
*Assistant Examiner* — David Bates
(74) *Attorney, Agent, or Firm* — Harness, Dickey

(57) ABSTRACT

An assembly tool comprises in an assembled configuration a proximal implant fastener, a distal implant fastener, and a compression member. The assembly tool is operable to hold in the assembled configuration a proximal implant partially engageable with a distal implant during implantation and axial impaction. Axial impaction is exerted through the compression member of the assembly tool. The assembly tool is also operable to securely lock the tapers of proximal and distal implants after impaction by rotating the compression member.

20 Claims, 14 Drawing Sheets

U.S. PATENT DOCUMENTS

| | | | |
|---|---|---|---|
| 5,092,900 A | 3/1992 | Marchetti et al. |
| 5,122,146 A | 6/1992 | Chapman et al. |
| 5,201,769 A | 4/1993 | Schutzer |
| 5,211,666 A | 5/1993 | Fetto |
| 5,409,492 A | 4/1995 | Jones et al. |
| 5,468,243 A | 11/1995 | Halpern |
| 5,489,284 A | 2/1996 | James et al. |
| 5,562,666 A | 10/1996 | Brumfield |
| 5,571,111 A | 11/1996 | Aboczky |
| 5,578,037 A | 11/1996 | Sanders et al. |
| 5,601,564 A | 2/1997 | Gustilo et al. |
| 5,607,431 A | 3/1997 | Dudasik et al. |
| 5,632,747 A | 5/1997 | Scarborough et al. |
| 5,645,549 A | 7/1997 | Boyd et al. |
| 5,649,930 A | 7/1997 | Kertzner |
| 5,665,090 A | 9/1997 | Rockwood et al. |
| 5,690,636 A | 11/1997 | Wildgoose et al. |
| 5,699,915 A | 12/1997 | Berger et al. |
| 5,704,940 A | 1/1998 | Garosi |
| 5,766,261 A | 6/1998 | Neal et al. |
| 5,788,701 A | 8/1998 | McCue |
| 5,849,015 A | 12/1998 | Haywood et al. |
| 5,860,969 A | 1/1999 | White et al. |
| 5,860,982 A | 1/1999 | Ro et al. |
| 5,908,423 A | 6/1999 | Kashuba et al. |
| 5,913,860 A | 6/1999 | Scholl |
| 5,976,145 A | 11/1999 | Kennefick, III |
| 5,989,261 A | 11/1999 | Walker et al. |
| 6,022,357 A | 2/2000 | Reu et al. |
| 6,027,505 A | 2/2000 | Peter et al. |
| 6,033,405 A | 3/2000 | Winslow et al. |
| 6,110,179 A | 8/2000 | Flivik et al. |
| 6,110,211 A | 8/2000 | Weiss |
| 6,117,138 A | 9/2000 | Burrows et al. |
| 6,117,173 A | 9/2000 | Taddia et al. |
| 6,126,694 A | 10/2000 | Gray, Jr. |
| 6,136,035 A | 10/2000 | Lob et al. |
| 6,139,551 A | 10/2000 | Michelson et al. |
| 6,143,030 A | 11/2000 | Schroder |
| 6,152,963 A | 11/2000 | Noiles et al. |
| RE37,005 E | 12/2000 | Michelson et al. |
| 6,159,216 A | 12/2000 | Burkinshaw et al. |
| 6,224,605 B1 | 5/2001 | Anderson et al. |
| 6,224,609 B1 | 5/2001 | Ressemann et al. |
| 6,238,435 B1 | 5/2001 | Meulink et al. |
| 6,245,111 B1 | 6/2001 | Shaffner |
| 6,267,785 B1 | 7/2001 | Masini |
| 6,302,890 B1 | 10/2001 | Leone, Jr. |
| 6,306,174 B1 | 10/2001 | Gie et al. |
| 6,330,845 B1 * | 12/2001 | Meulink .................. 81/462 |
| 6,338,734 B1 | 1/2002 | Burke et al. |
| 6,344,060 B1 | 2/2002 | Schmotzer et al. |
| 6,361,565 B1 | 3/2002 | Bonutti |
| 6,371,991 B1 | 4/2002 | Manasas et al. |
| 6,395,004 B1 | 5/2002 | Dye et al. |
| 6,468,281 B1 | 10/2002 | Badorf et al. |
| 6,517,581 B2 | 2/2003 | Blamey |
| 6,626,913 B1 | 9/2003 | McKinnon et al. |
| 6,871,549 B2 | 3/2005 | Serra et al. |
| 6,883,217 B2 | 4/2005 | Barrette et al. |
| 6,913,623 B1 | 7/2005 | Zhu |
| 6,932,819 B2 | 8/2005 | Wahl et al. |
| 7,074,224 B2 | 7/2006 | Daniels et al. |
| 7,179,259 B1 | 2/2007 | Gibbs |
| 7,210,881 B2 | 5/2007 | Greenberg |
| 7,247,171 B2 | 7/2007 | Sotereanos |
| 7,255,716 B2 | 8/2007 | Pubols et al. |
| 7,291,176 B2 | 11/2007 | Serra et al. |
| 7,297,166 B2 | 11/2007 | Dwyer et al. |
| 7,341,589 B2 | 3/2008 | Weaver et al. |
| 7,425,214 B1 | 9/2008 | McCarthy et al. |
| 7,491,242 B2 | 2/2009 | Pichon et al. |
| 7,582,092 B2 | 9/2009 | Jones et al. |
| 7,585,301 B2 | 9/2009 | Santarella et al. |
| 7,832,405 B1 * | 11/2010 | Schlueter et al. ............ 128/898 |
| 8,221,432 B2 * | 7/2012 | Smith et al. .................... 606/99 |
| 2003/0233100 A1 * | 12/2003 | Santarella et al. ............. 606/99 |
| 2004/0107001 A1 | 6/2004 | Cheal et al. |
| 2004/0122439 A1 | 6/2004 | Dwyer et al. |
| 2004/0236341 A1 | 11/2004 | Petersen |
| 2005/0203539 A1 | 9/2005 | Grimm et al. |
| 2007/0093844 A1 | 4/2007 | Dye |
| 2007/0123908 A1 | 5/2007 | Jones et al. |
| 2007/0129809 A1 | 6/2007 | Meridew et al. |
| 2008/0125867 A1 | 5/2008 | McCleary et al. |
| 2008/0154276 A1 | 6/2008 | Pubols et al. |
| 2008/0161811 A1 | 7/2008 | Daniels et al. |
| 2008/0208203 A1 | 8/2008 | Moindreau et al. |
| 2008/0234685 A1 | 9/2008 | Gjerde |
| 2008/0269765 A1 | 10/2008 | Banerjee et al. |
| 2008/0294168 A1 | 11/2008 | Wieland |
| 2009/0099566 A1 | 4/2009 | Maness et al. |
| 2009/0112218 A1 | 4/2009 | McCleary et al. |
| 2009/0265014 A1 | 10/2009 | May et al. |

FOREIGN PATENT DOCUMENTS

| | | |
|---|---|---|
| FR | 2676172 A1 | 11/1992 |
| GB | 2299758 A | 10/1996 |
| WO | WO-94/21199 A1 | 9/1994 |
| WO | WO-2007/106752 A2 | 9/2007 |

OTHER PUBLICATIONS

Zimmer, Inc., "ZMR Hip System", 2004, 19sheets.

* cited by examiner

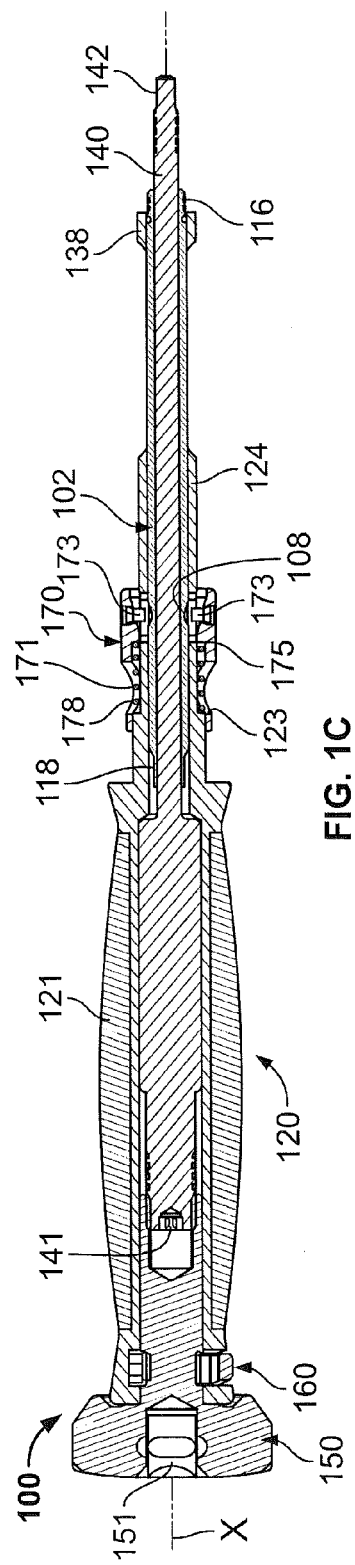
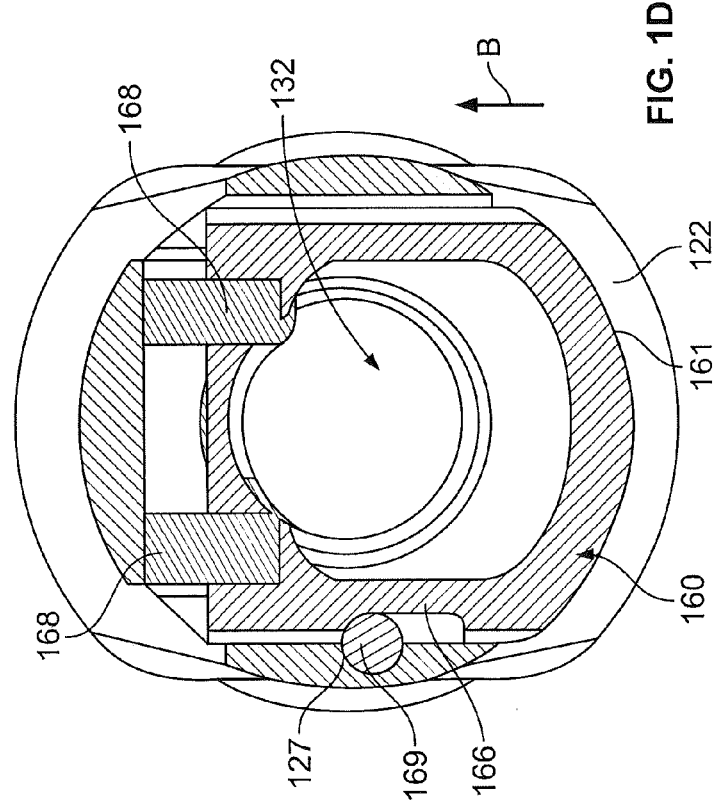
FIG. 1C
FIG. 1D

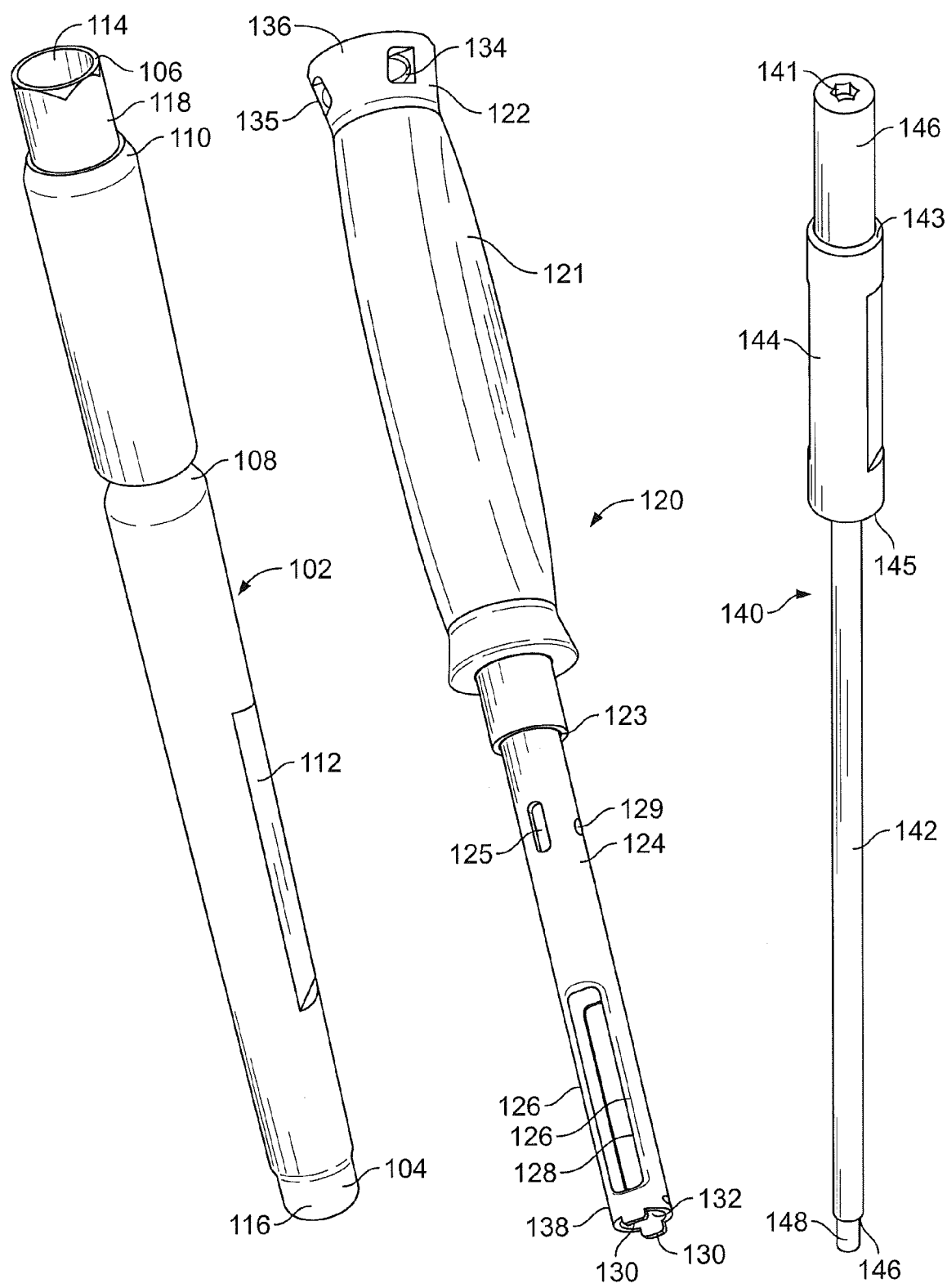

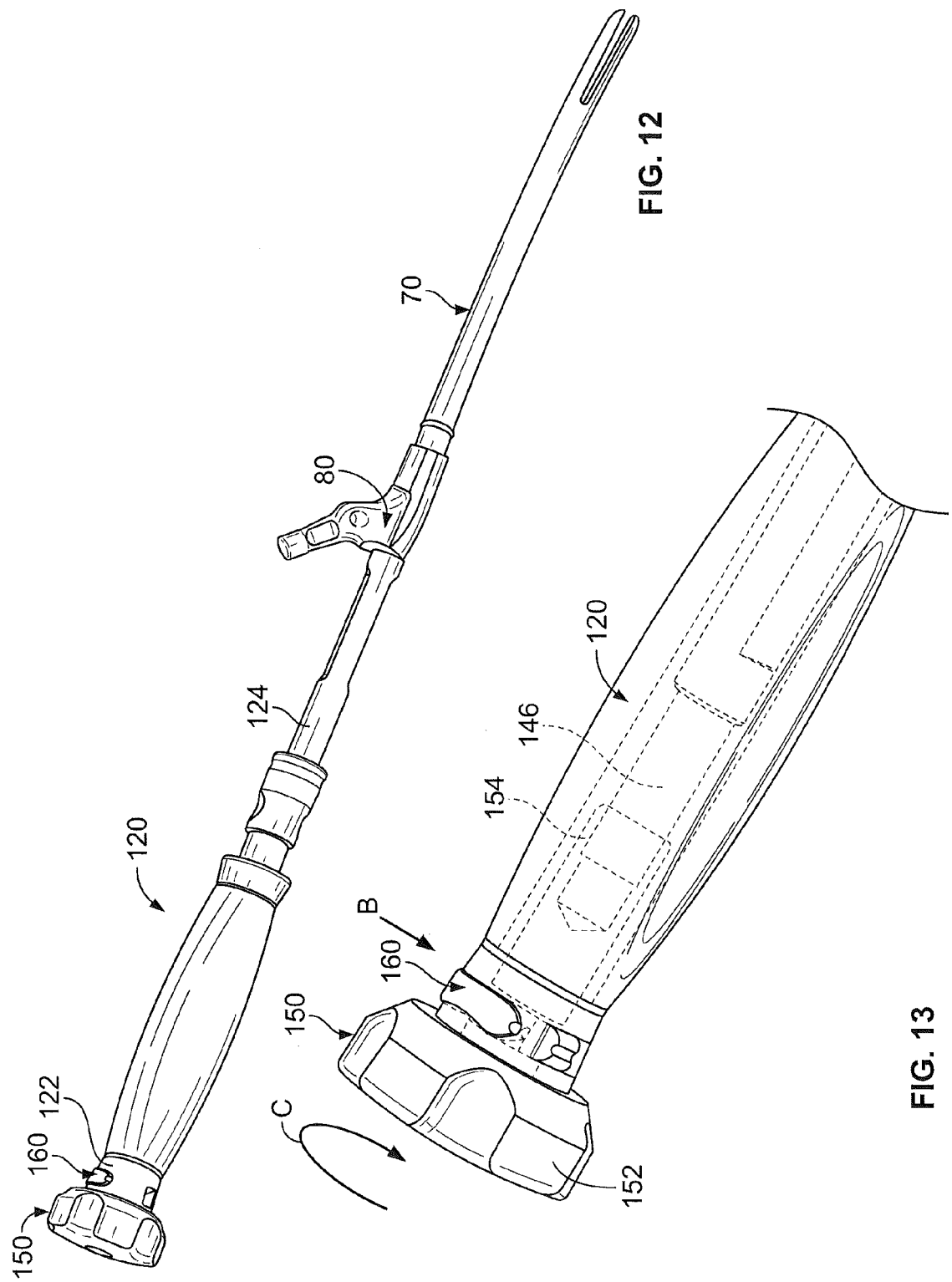

ASSEMBLY TOOL FOR MODULAR IMPLANTS AND ASSOCIATED METHOD

CROSS-REFERENCE TO RELATED APPLICATIONS

This application is related to U.S. patent application Ser. No. 12/718,018 filed Mar. 5, 2010, now U.S. Pat. No. 8,221, 432 issued Jul. 17, 2012, entitled "METHOD AND APPARATUS FOR IMPLANTING A MODULAR FEMORAL HIP;" U.S. patent application Ser. No. 12/718,230 filed Mar. 5, 2010, entitled "MODULAR LATERAL HIP AUGMENTS;" U.S. patent application Ser. No. 12/718,023 filed Mar. 5, 2010, entitled "GUIDE ASSEMBLY FOR LATERAL IMPLANTS AND ASSOCIATED METHODS;" U.S. patent application Ser. No. 12/718,026 filed Mar. 5, 2010, entitled "REVISION BROACH WITH SMOOTH LATERAL SIDE;" and U.S. patent application Ser. No. 12/718, 031 filed Mar. 5, 2010, entitled "METHOD AND APPARATUS FOR TRIALING AND IMPLANTING A MODULAR FEMORAL HIP;" each filed concurrently herewith. The disclosures of each of the above applications are incorporated herein by reference.

INTRODUCTION

In femoral revision arthroplasty modular implants having separate proximal and distal components are often used. The proximal and distal components can be inserted using known assembly tools, which are then removed before locking the components together.

The present teachings provide an assembly tool for inserting and locking proximal and distal components of a modular implant.

SUMMARY

The present teachings provide an assembly tool having a proximal implant fastener, a distal implant fastener, and a compression member. The assembly tool is operable to hold in the assembled configuration a proximal implant partially engageable with a distal implant during implantation and axial impaction. Axial compaction can be exerted through the compression member of the assembly tool. The assembly tool is also operable to securely lock the tapers of the proximal and distal implants after impaction by rotating the compression member.

The present teachings also provide an assembly tool comprising a first coupler a handle member, a second coupler and a compression member. The first coupler has a first longitudinal shaft defining a first longitudinal bore and can be engaged to a proximal implant of a modular implant assembly. The handle member is removably couplable with the first coupler and the first coupler is received in a longitudinal bore of the handle member. The second coupler has a second longitudinal shaft passable through the first longitudinal bore of the first coupler. The second longitudinal shaft can be engageable to a distal implant of the modular implant through the proximal implant. The proximal implant and the distal implant are connectable with corresponding tapers. The compression member can be coupled to a proximal portion of the second longitudinal shaft and has an impaction surface. The compression member is operable to insert the proximal and distal implants to the anatomic site by impaction while holding the tapers at a selected separation distance. The compression member includes a knob. The knob is rotatable to reduce the separation distance and lock corresponding tapers of the proximal and distal implants after impaction.

The present teachings provide a method of implanting a modular implant having a proximal implant and a distal implant into an anatomic site. In one aspect, the method includes sequentially assembling a plurality of components of an assembly tool on to the proximal and distal implants and holding corresponding tapers of the proximal and distal implants separated by a selected distance by the assembly tool. The method also includes impacting the proximal and distal implants to an anatomic depth without changing the separation distance by impacting the assembly tool, and actuating the assembly tool to lock the corresponding tapers of proximal and distal implant without removing the assembly tool.

In another aspect, the method includes engaging a distal portion of first coupler to an inner bore of the proximal implant, releasably connecting a handle member over the first coupler, passing a second coupler through the handle member and the first coupler and connecting the proximal and distal implants. The method also includes engaging a distal portion of the second coupler through the proximal implant to the distal implant, engaging a compression member to a proximal portion of the second coupler through the handle member, and rotating the compression member to hold corresponding tapers of the proximal and distal implants separated by a selected distance. The method also includes impacting the proximal and distal implants to an anatomic depth by impacting the compression member while holding the tapers separated by the selected distance, and rotating the compression member to lock the corresponding tapers of proximal and distal implant without removing the compression member.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 1C is a sectional view of the assembly tool of FIG. 1A taken along C-C;

FIG. 1D is a sectional view of the assembly tool of FIG. 1B taken along D-D;

FIG. 2 is an isometric view of a proximal implant fastener of the assembly tool of FIG. 1;

FIG. 3 is an isometric view of a handle member of the assembly tool of FIG. 1;

FIG. 4 is an isometric view of a distal implant fastener of the assembly tool of FIG. 1;

FIG. 12 is an isometric view illustrating the fully assembled assembly tool holding the proximal and distal implants together according to the present teachings;

FIG. 13 is a detail of FIG. 12, illustrating rotating a compression member of the assembly tool until an audible sound is heard according to the present teachings;

DESCRIPTION OF VARIOUS ASPECTS

Figure 1:
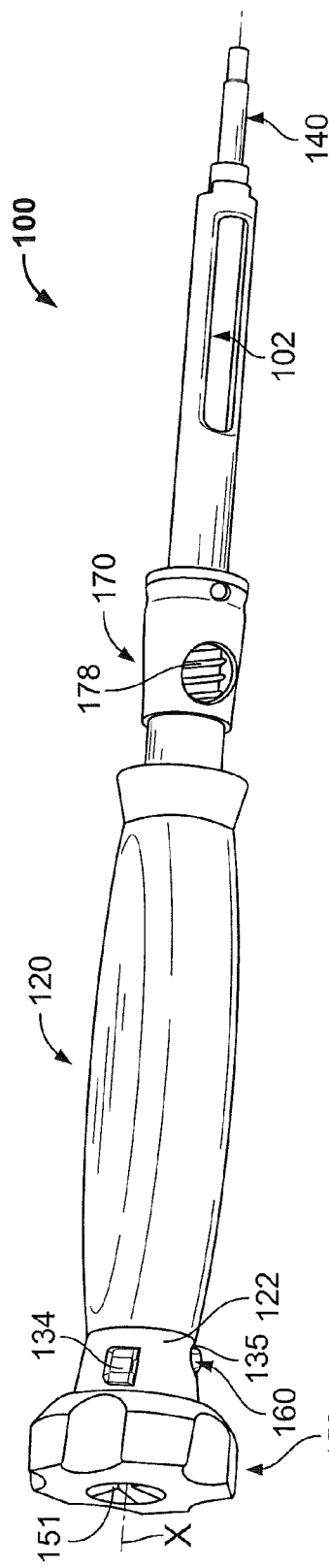
FIG. 1 is an isometric view of an assembly tool according to the present teachings.
Figure 1A:
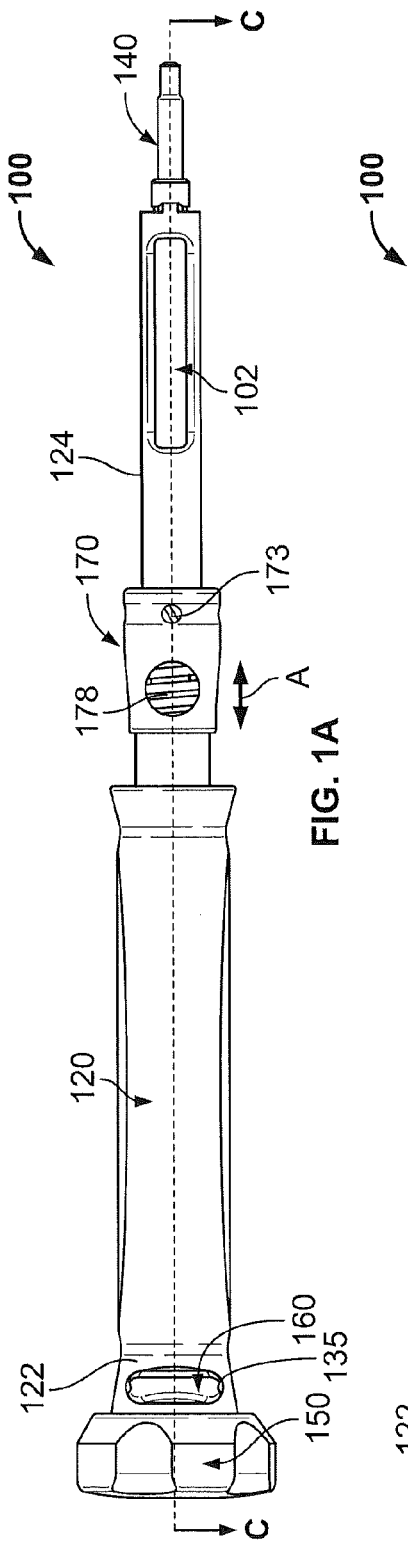
FIG. 1A is a side view of the assembly tool of FIG. 1.
Figure 1B:
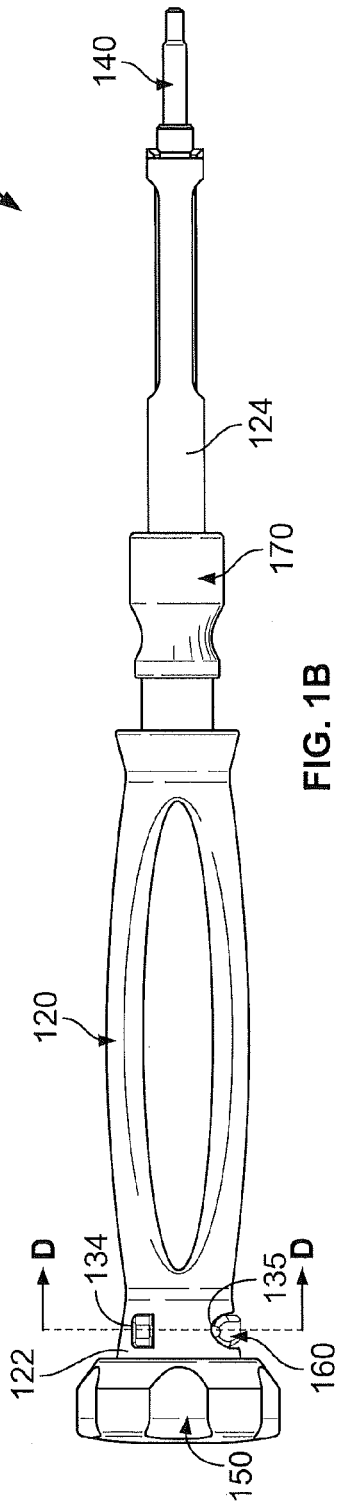
FIG. 1B is a plan view of the assembly tool of FIG. 1.
Figure 5:
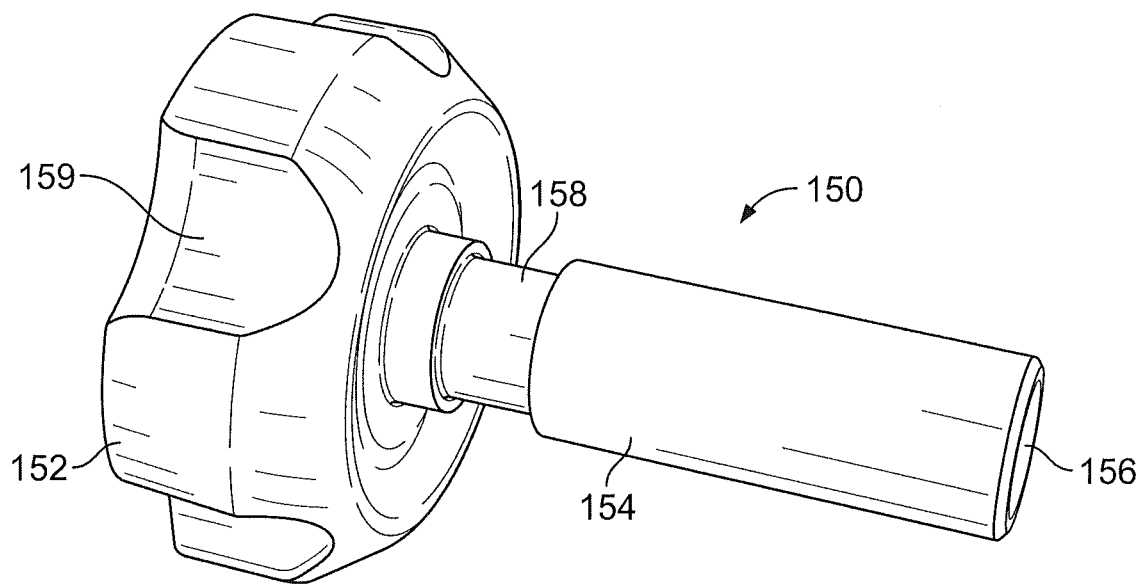
FIG. 5 is an isometric view of a compression member of the assembly tool of FIG. 1.
Figure 6:
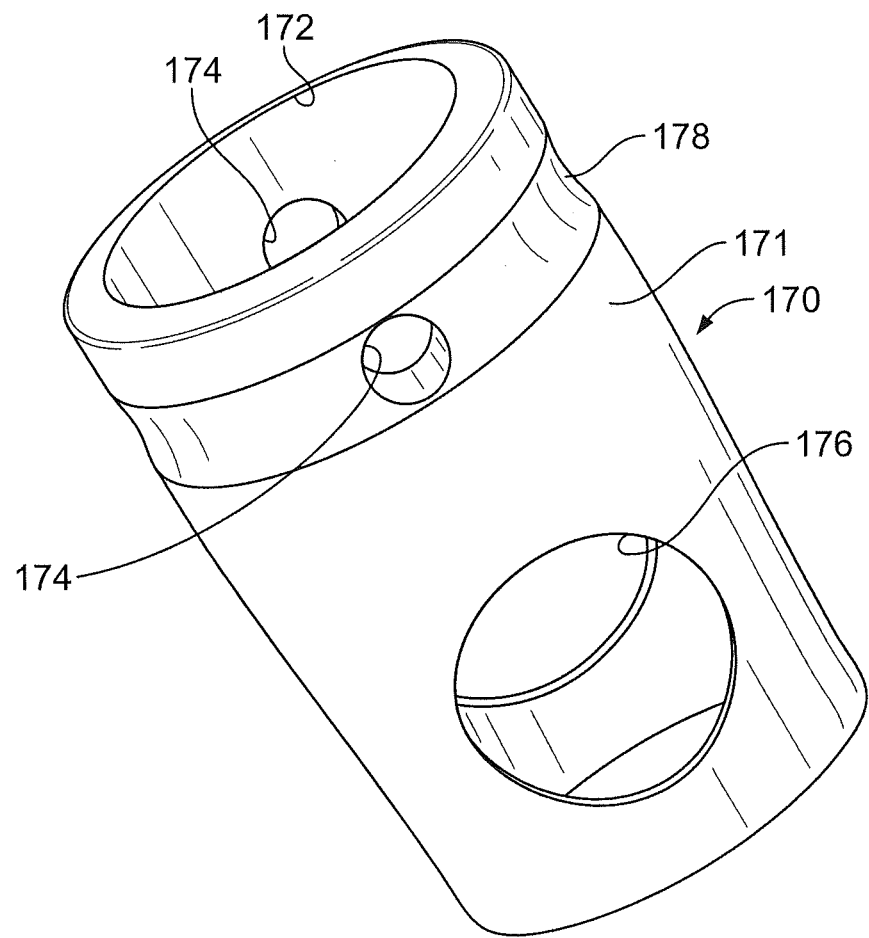
FIG. 6 is an isometric view of a sleeve of the assembly tool of FIG. 1.
Figure 7:
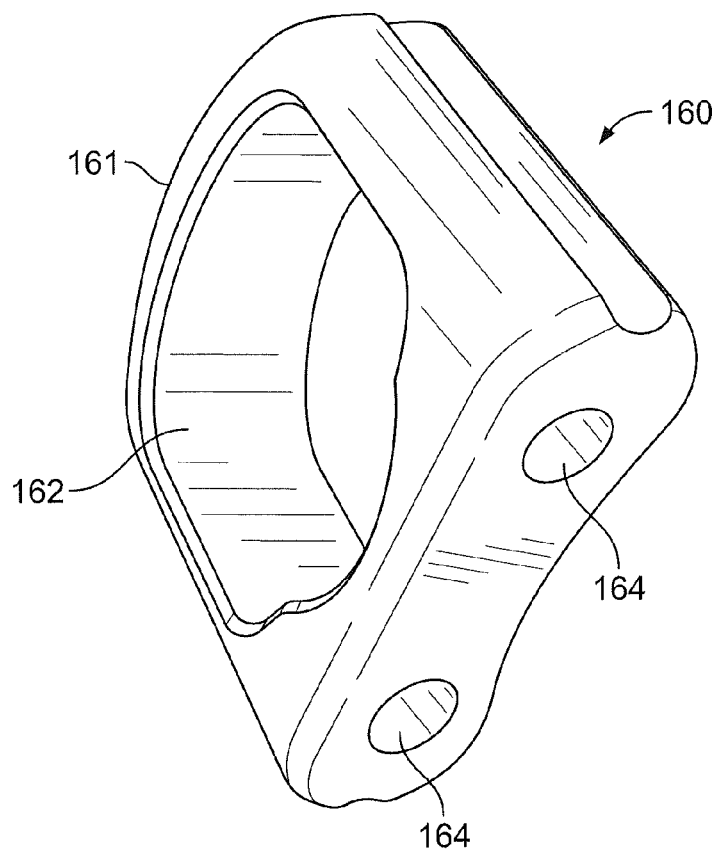
FIG. 7 is first isometric view of a slider fastener of the assembly tool of FIG. 1.

The following description is merely exemplary in nature and is in no way intended to limit the present teachings, applications, or uses. For example, although the present teachings are illustrated for hip joints in femoral revision systems, the present teachings can be used for assembling and locking modular implants for modular systems implantable in other joints, such as the knee or shoulder.

Referring to FIGS. 1, 1A-1D and 2-7, an exemplary assembly tool 100 according to the present teachings is illustrated. The assembly tool 100 can include a plurality of modularly connected components, which can be assembled onto a modular implant sequentially and, after implantation, disassembled in reverse order. The assembly tool 100 can include a handle member 120, a first coupler or proximal implant fastener 102, a second coupler or distal implant fastener 140, a slider 160, a locking member 170 and a compression cap or a compression member 150.

The handle member 120 can extend from a proximal end 136 to a distal end 138 along a longitudinal axis X and can include a handle portion 121 and a tubular shaft 124. The handle portion 121 can be molded over the tubular shaft 124, as shown in FIG. 3. Alternatively, the handle portion 121 can be removably attached to the tubular shaft 124. A through bore 132 extends through the handle member 120 from the proximal end 136 to the distal end 138 of the handle member 120. The tubular shaft 124 can include an elongated through slot 128 defined by a pair of arms 126 connected at the distal end 138. First and second anti-rotation tabs 130 can extend from the distal end 138. The anti-rotation tabs 130 allow version control during implantation, as discussed below. A proximal portion 122 of the handle member 120 can be configured for removably coupling with the compression member 150 and with the slider 160, as discussed below. The proximal portion 122 can define openings 134 facilitating cleaning and sterilizing of the handle member 120.

Figure 8:
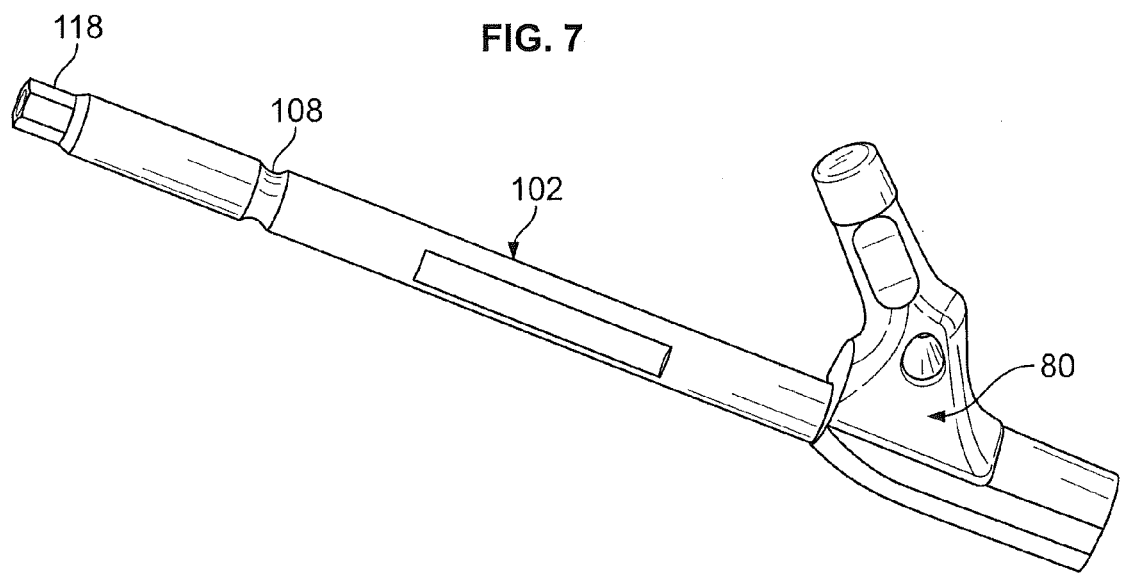
FIG. 8 is an isometric view illustrating the proximal implant fastener of FIG. 2 engaging the proximal implant according to the present teachings.
Figure 7A:
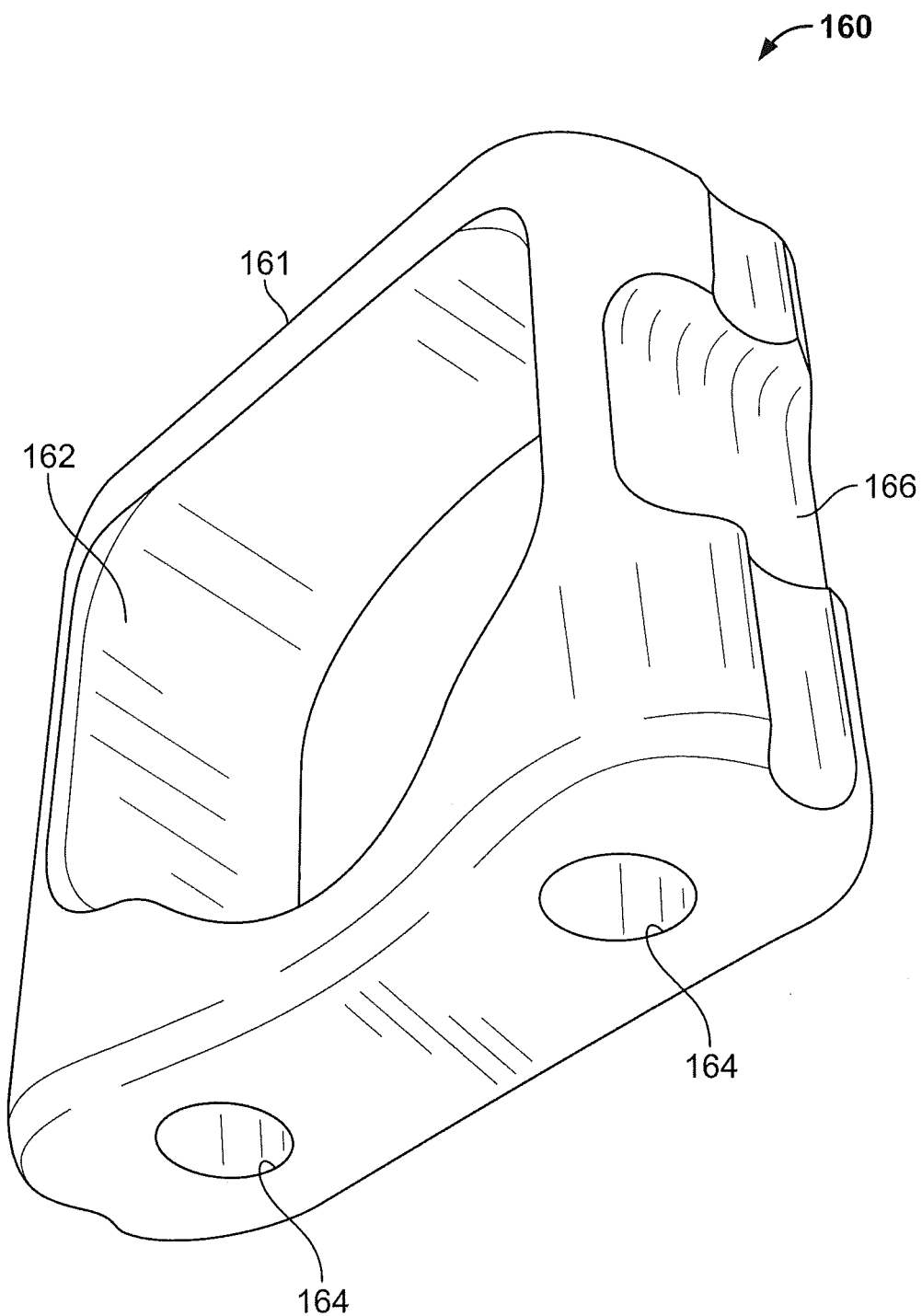
FIG. 7A is a second isometric view of a slider fastener of the assembly tool of FIG. 1.
Figure 9:
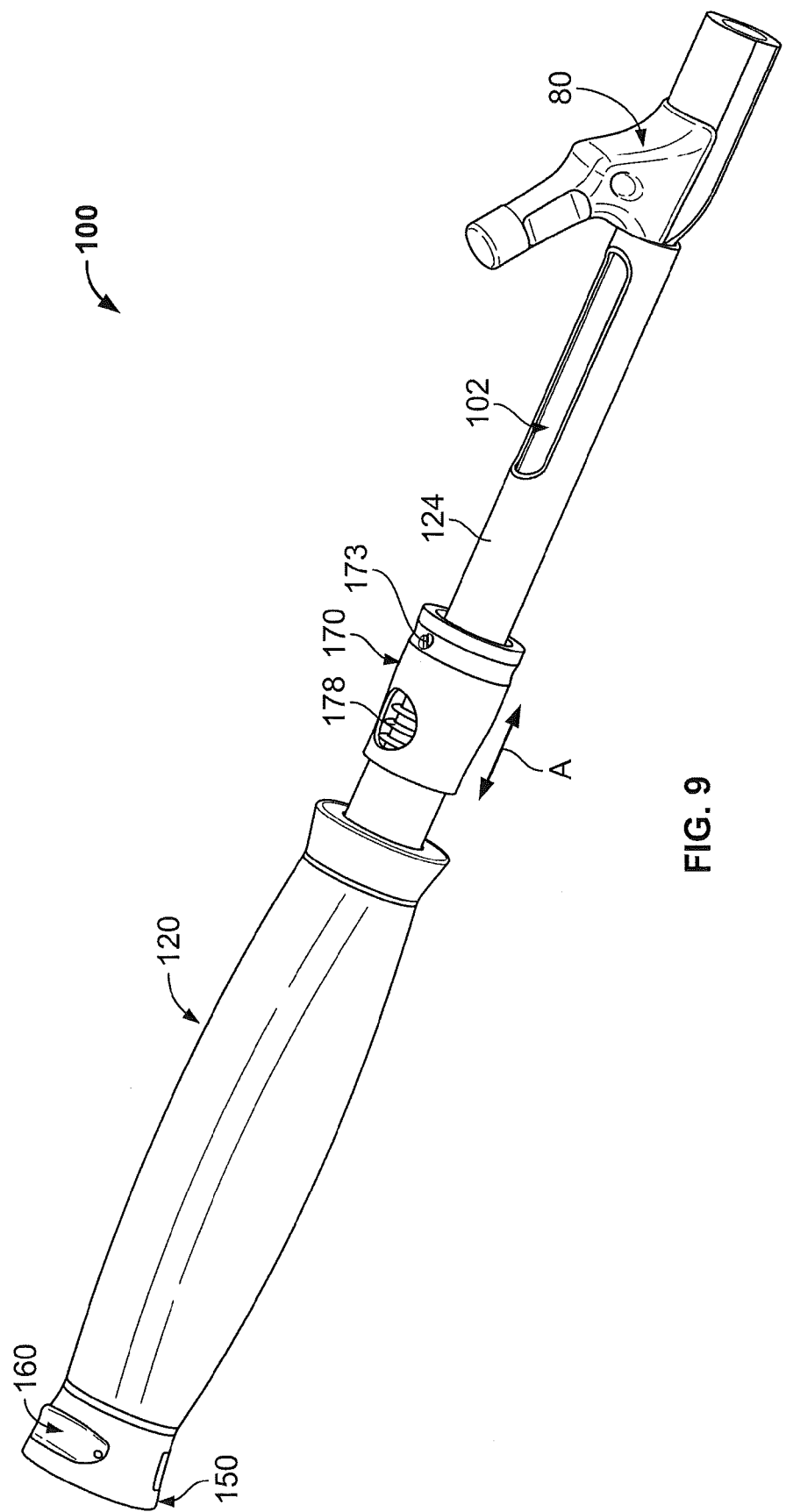
FIG. 9 is an isometric view illustrating the handle member of FIG. 3 assembled over the proximal implant fastener according to the present teachings.
Figure 15:
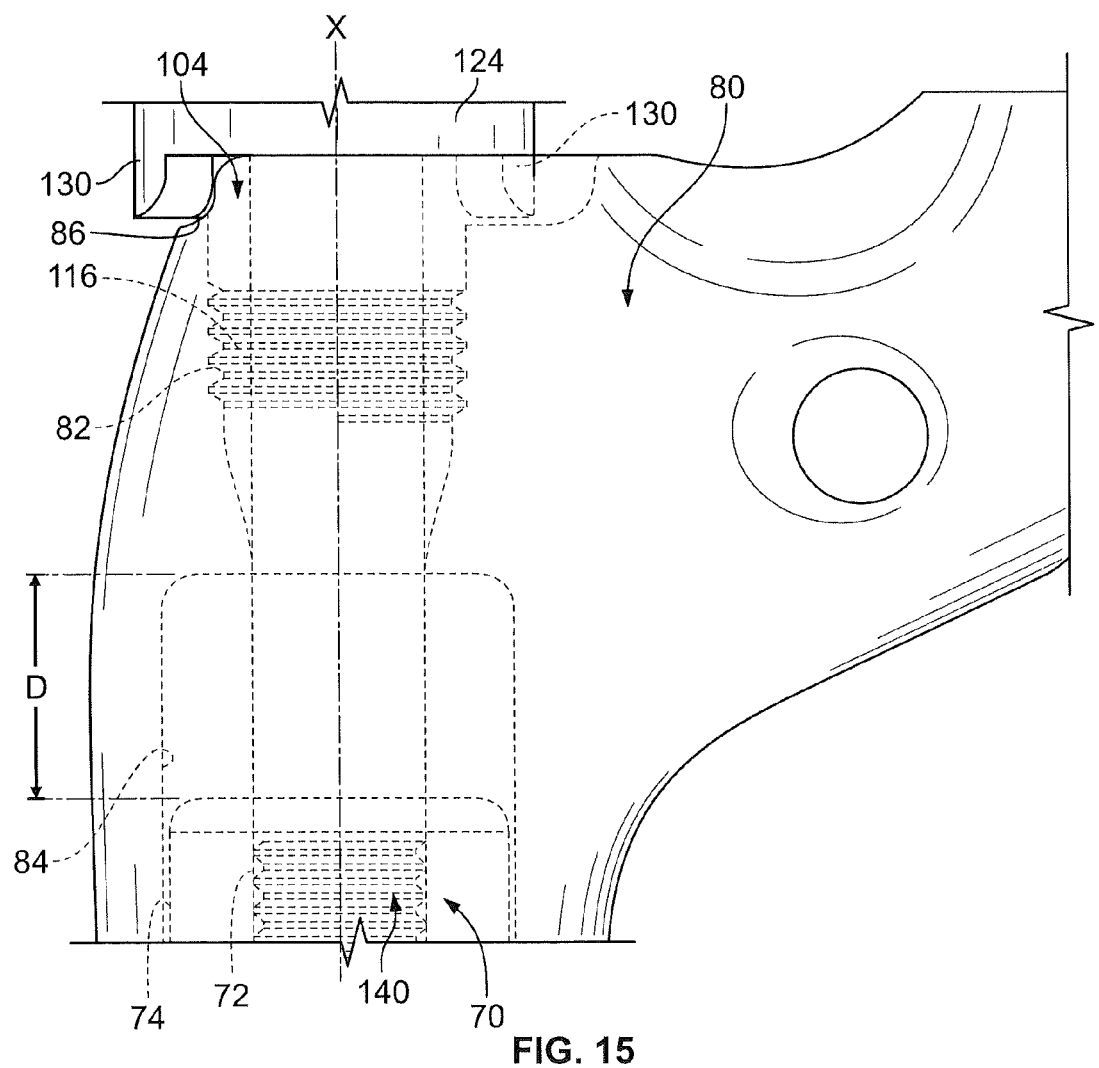
FIG. 15 is a detail of the fully assembled assembly view of FIG. 14, illustrating a separation distance between corresponding tapers of the proximal and distal implants.

Referring to FIG. 2, the first coupler 102 can be a tubular shaft extending between a proximal end 106 and a distal end 104 and having an internal through bore 114. The first coupler 102 can include an external circumferential groove 108 for removable coupling with the handle member 120 and the locking member 170, as discussed below. A distal portion 116 of the first coupler 102 can be configured for coupling to a first or proximal implant 80 of a modular implant assembly, as shown in FIGS. 8 and 15. The distal portion 116 can be, for example, externally threaded and threadably engageable with an internally threaded bore 82 of the proximal implant 80. The first coupler 102 can be engaged to the proximal implant 80 by engaging the distal portion 116 of the first coupler 102 to a bore 82 of the proximal implant 80 (shown in FIG. 15). The first coupler 102 can be rotated either manually or by using a driver to engage a driver-engageable proximal portion 118 of the first coupler 102, as shown in FIG. 8. The first coupler 102 and the proximal implant 80 can be threadably engaged, as illustrated in FIG. 15, although other coupling engagements can also be used. The handle member 120 can be positioned concentrically over the first coupler 102 through the bore 132 of the handle member 120, such that the first coupler 102 is received in the bore 132. The handle member 120 can be locked onto the first coupler 102 by axially moving the quick-connect locking member 170, as shown in FIGS. 9 and 10 and discussed below.

Figure 10:
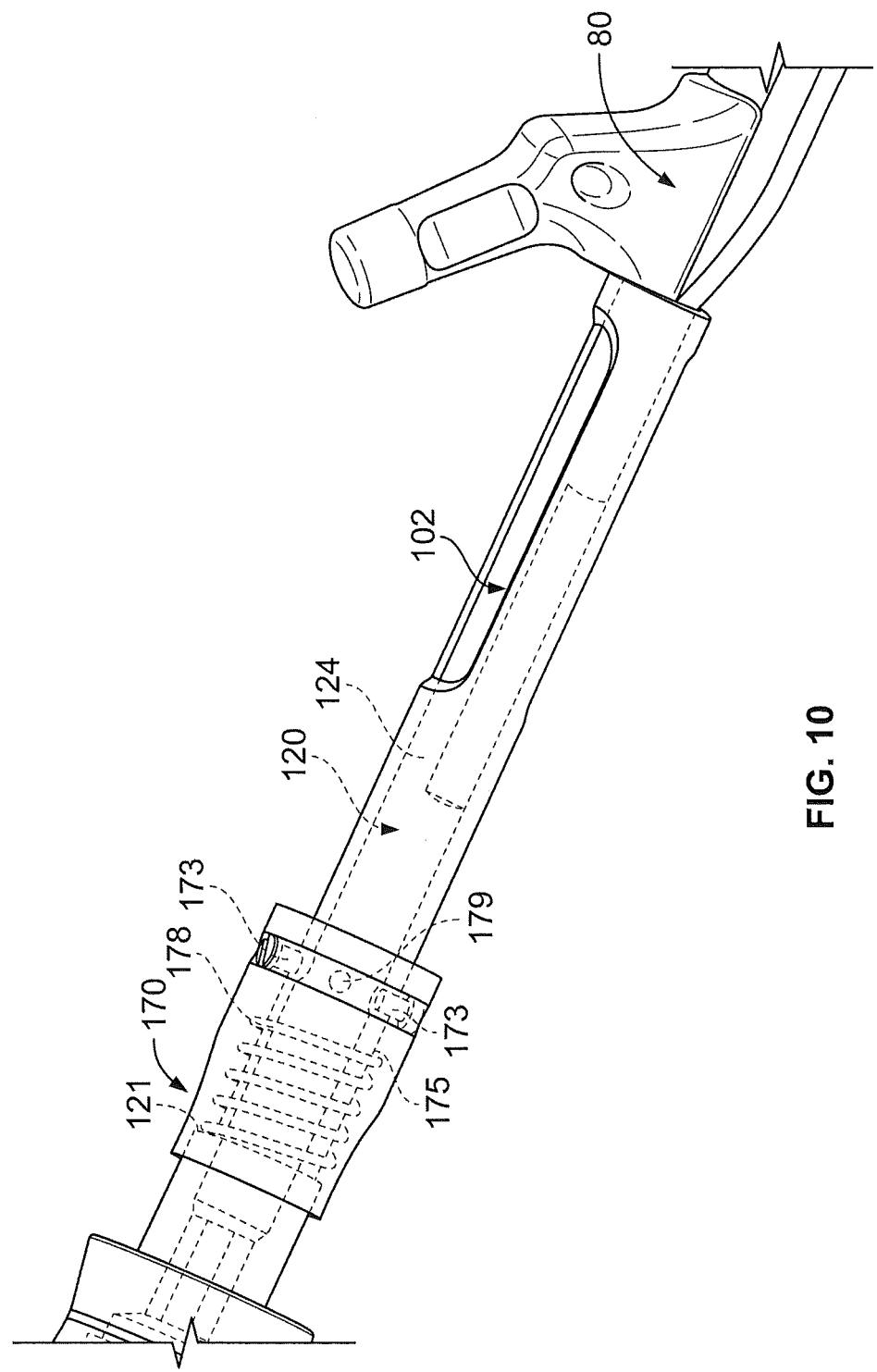
FIG. 10 is an isometric view of a detail of FIG. 9 illustrating a locking member between the handle member and the proximal implant fastener according to the present teachings.

Referring to FIGS. 1, 1A-1C, 6, 9 and 10, the locking member 170 can include a sleeve 171 having a longitudinal bore 172. The sleeve 171 can be spring-loaded onto to the handle member 120 with a spring 178 received within the bore 172 of the sleeve 171 over the tubular shaft 124 of the handle member 120. The spring 178 can be constrained in the sleeve 171 between a circumferential outer shoulder 123 of the handle member 120 and a circumferential inner shoulder 175 of the sleeve 171. The sleeve 171 can be movably supported on the shaft 124 of the handle member 120 along the longitudinal direction of the handle member 120, as indicated with double arrow A in FIG. 1A. In the exemplary embodiment illustrated in FIGS. 1A-1D and 10, a pair of diametrically opposed set screws or pins 173 can pass through holes 174 of the sleeve 171 and through elongated through slots 125. The pins 173 allow the sleeve 171 to move against the bias of the spring 178 relative to the first coupler 102 until a pair of ball bearings 179 engage the groove 108 of the first coupler 102 through holes 129 of the shaft 124 of the handle member 120 to lock the first coupler 102 to the handle member 120. The ball bearings 179 can be positioned within the sleeve 171 circumferentially at 90 degrees relative to the pins 173, as shown in FIGS. 3 and 10. The locking member 170 releasably couples the handle member 120 to the first coupler 102 in a quick-release manner.

Referring to FIGS. 7, 1A-1D and 9, the handle member 120 can be assembled with a slider 160, which defines an eccentric or asymmetric opening 162. The slider 160 is supported within the handle member 120 and is held against the action of two springs 168 by a dowel 169, as shown in FIG. 1D. The dowel 169 is received through a top opening 127 of the distal portion 122 of the handle member 120 and is held against an external slot 166 of the slider 160. The slider 160 can partially obstruct the longitudinal bore 132 of the handle member, as shown in FIG. 1D. A curved portion 161 of the slider 160 extends through an arcuate slot 135. The curved portion 161 can be pushed inward in the direction of arrow B against the action of the springs 168, such that the bore 132 is not obstructed. The function of the slider 160 is further discussed below.

Figure 11:
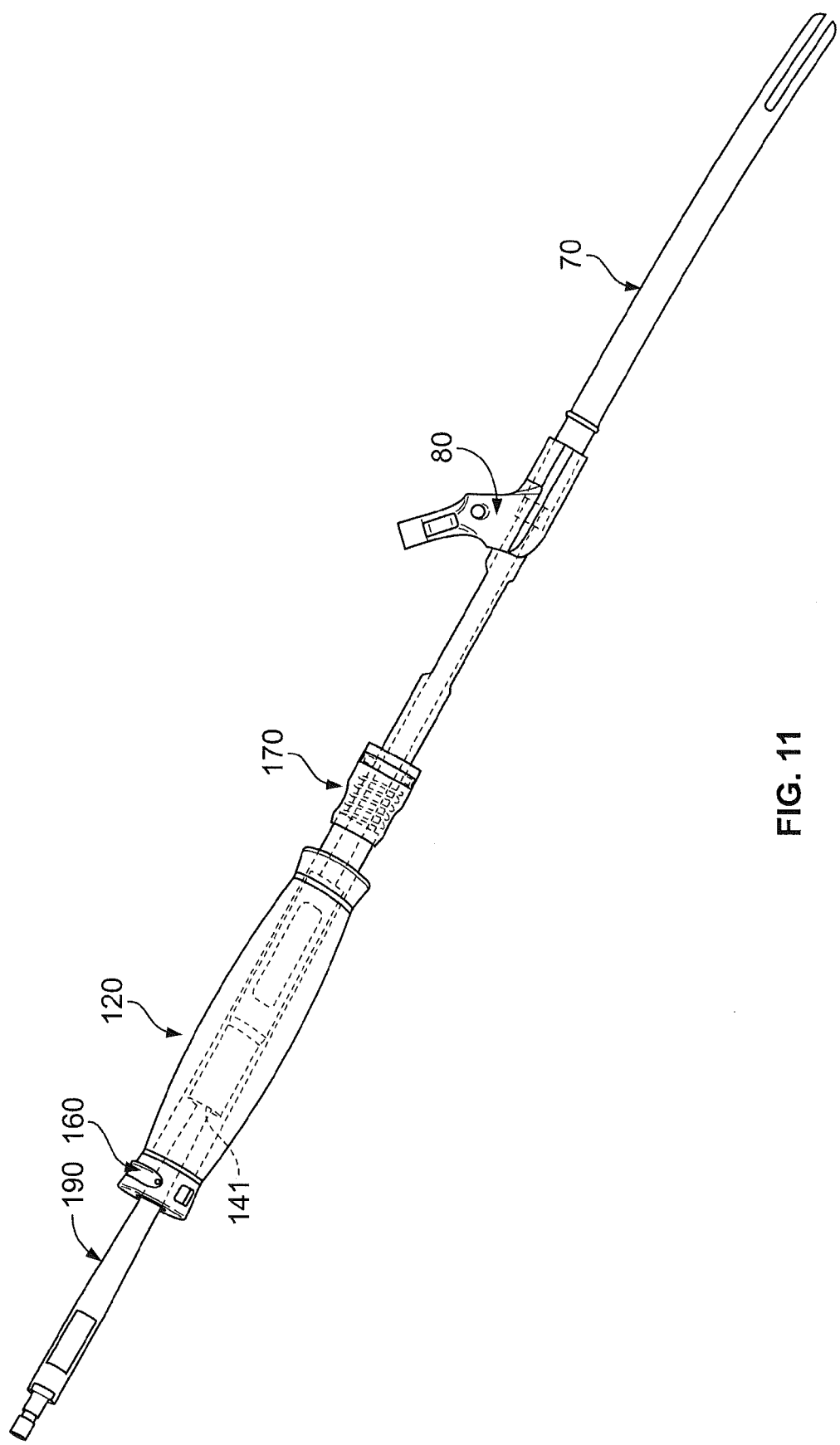
FIG. 11 is an isometric view illustrating the distal implant fastener engaging a distal implant through the assembly of FIG. 9 according to the present teachings.

Referring to FIGS. 4, 1A-1D, and 11-13, the second coupler 140 can include a proximal shaft portion 146, an intermediate shaft portion 144, a distal shaft portion 142 and an externally threaded distal tip portion 148. The various portions 146, 144, 142, 148 can have different diameters, such that corresponding shoulders 143, 145 and 146 are defined therebetween, as shown in FIG. 4. The proximal shaft portion 146 can be externally threaded for engaging the compression member 150, as discussed below. The proximal and distal implants 80, 70 can be aligned and held manually against one another. The second coupler 140 can be concentrically received through the handle member 120, through the bore 114 of the first coupler 102 and through the proximal implant 80 to engage a second or distal implant 70 for coupling the proximal implant 80 and the distal implant 70 of the modular implant assembly, as illustrated in FIG. 11. A driver 190 can be used to engage a driver engagement formation 141 of the proximal shaft portion 146 of the second coupler 140 and rotatably engage the threaded distal tip portion 148 to internal threaded bore 72 of a distal implant 70, as illustrated in FIGS. 11 and 15.

Figure 14:
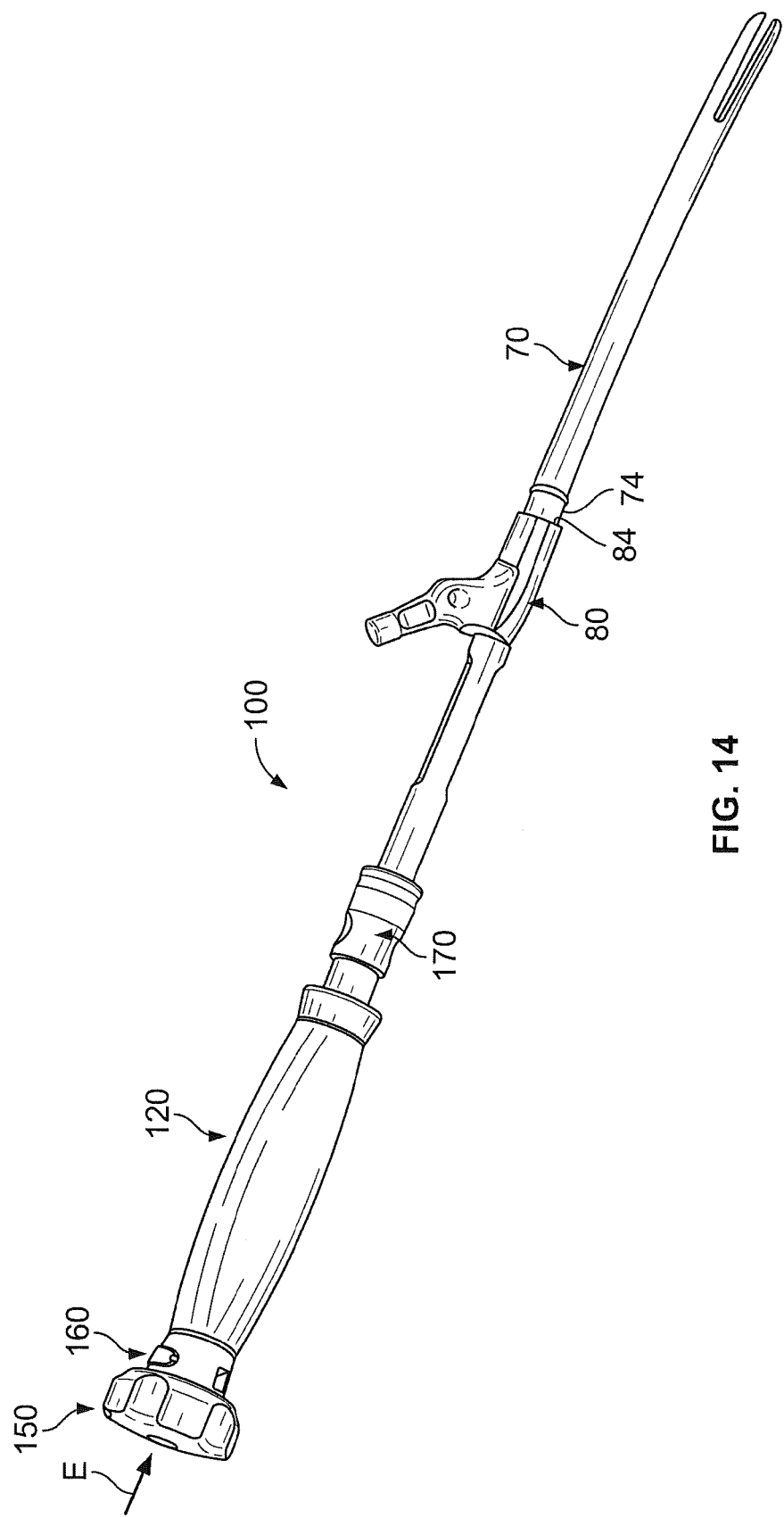
FIG. 14 is an isometric view illustrating the fully assembled assembly tool during impaction according to the present teachings.

As illustrated in FIGS. 12, 14 and 15, the proximal implant 80 can be a proximal femoral body and the distal implant 70 can be a distal femoral stem 70. The proximal and distal implants 80, 70 can include corresponding female and male interlocking tapers 84, 74. As shown in FIG. 15, the interlocking tapers 84, 74 can remain separated and not fully locked during insertion.

Referring to FIGS. 5, 1A-1D and 12-13, the compression member 150 can include a knob portion 152 and a tubular shaft 154. The knob portion 152 can include thumb grooves 159 or other engagement features for rotating the compression member 150. The knob portion 152 can also include an attachment recess 151 for engaging a driver, such as a wrench. The compression member 150 can also include a circumferential groove 158, which can engage the slider 160, as discussed below. The shaft 154 of the compression member 150 can include an internal threaded bore 156, which can be threadably engaged with the externally threaded proximal shaft portion 146 of the second coupler 140. Pushing the slider 160 inward in the direction of arrow B, allows the tubular shaft 154 to be inserted through the longitudinal bore 132 of the handle member 120, as described in connection with FIG. 1D above.

With continued reference to FIGS. 12 and 13, by rotating the knob portion 152 in the direction of curved arrow C, the tubular shaft 154 moves longitudinally and threadably engages the tubular shaft 154 to the proximal shaft portion 146 of the second coupler 140. When the tubular shaft 154 is threaded to the proximal shaft portion 146 along a predetermined length, the slider 160 reaches the level of the circumferential groove 158 and springs into engagement with the circumferential groove 158 with an audible sound or click. The audible sound can signify that the assembly tool 100 is assembled onto the proximal and distal implants 80 and 70, holding the proximal and distal implants at a relative position or distance for implantation. As discussed above, the assembled proximal and distal implants 80, 70 are kept with their respective female and male tapers 84, 74 separated by a distance "D" and are not fully locked, as shown in FIG. 15. The assembly tool 100 can be used to insert the proximal and distal implants 80, 70 into the prepared anatomic site, such as, for example, the patient's femoral bone.

As shown in FIG. 14, the proximal and distal implants 80, 40 can be implanted by axially impacting the upper surface of the compression member 150 in the direction of arrow E. While the assembly tool 100 is impacted in situ and moves such that the distal implant 70 reaches a final seated depth in the anatomic site, version control is available for selection by the medical professional. In particular, the anti-rotational tabs 130 of the handle member 120 can engage corresponding slots 86 defined on the proximal outer surface of the proximal implant 80, such that rotating the handle portion 121 of the handle member 120 about the longitudinal axis X during axial impaction can rotate the handle member 120 and the attached the proximal implant 80 until a selected rotational orientation or version about the axis X is achieved. Impaction does not affect the separation distance D of the female and male tapers 84, 74 of the proximal and distal implants 80, 70 which are held apart by the structural features of the slider 160, the compression member 150 and the first and second couplers 102, 140, as discussed above.

Figure 16:
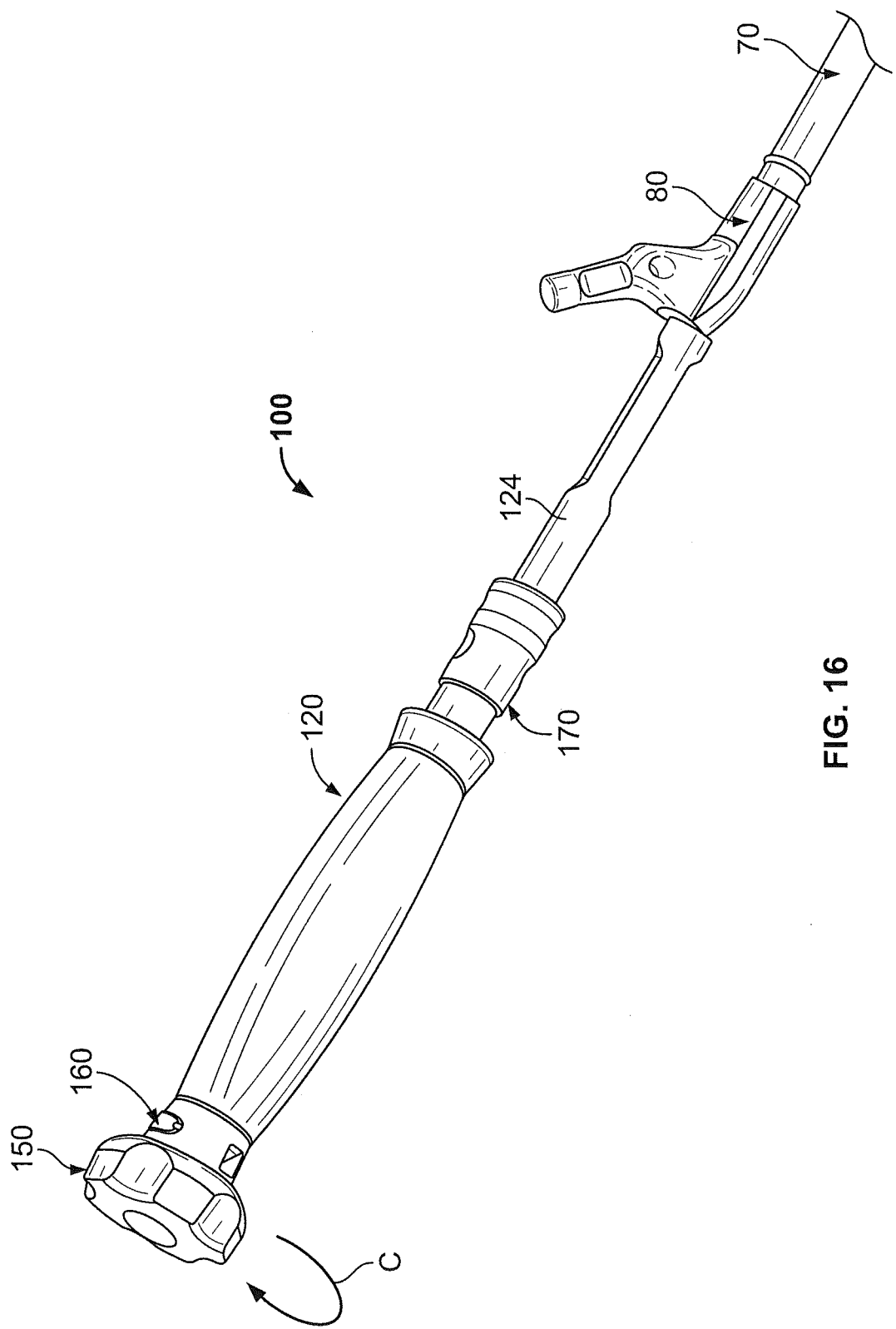
FIG. 16 is an isometric view illustrating the rotation of a compression member of the assembly tool after impaction according to the present teachings.
Figure 17:
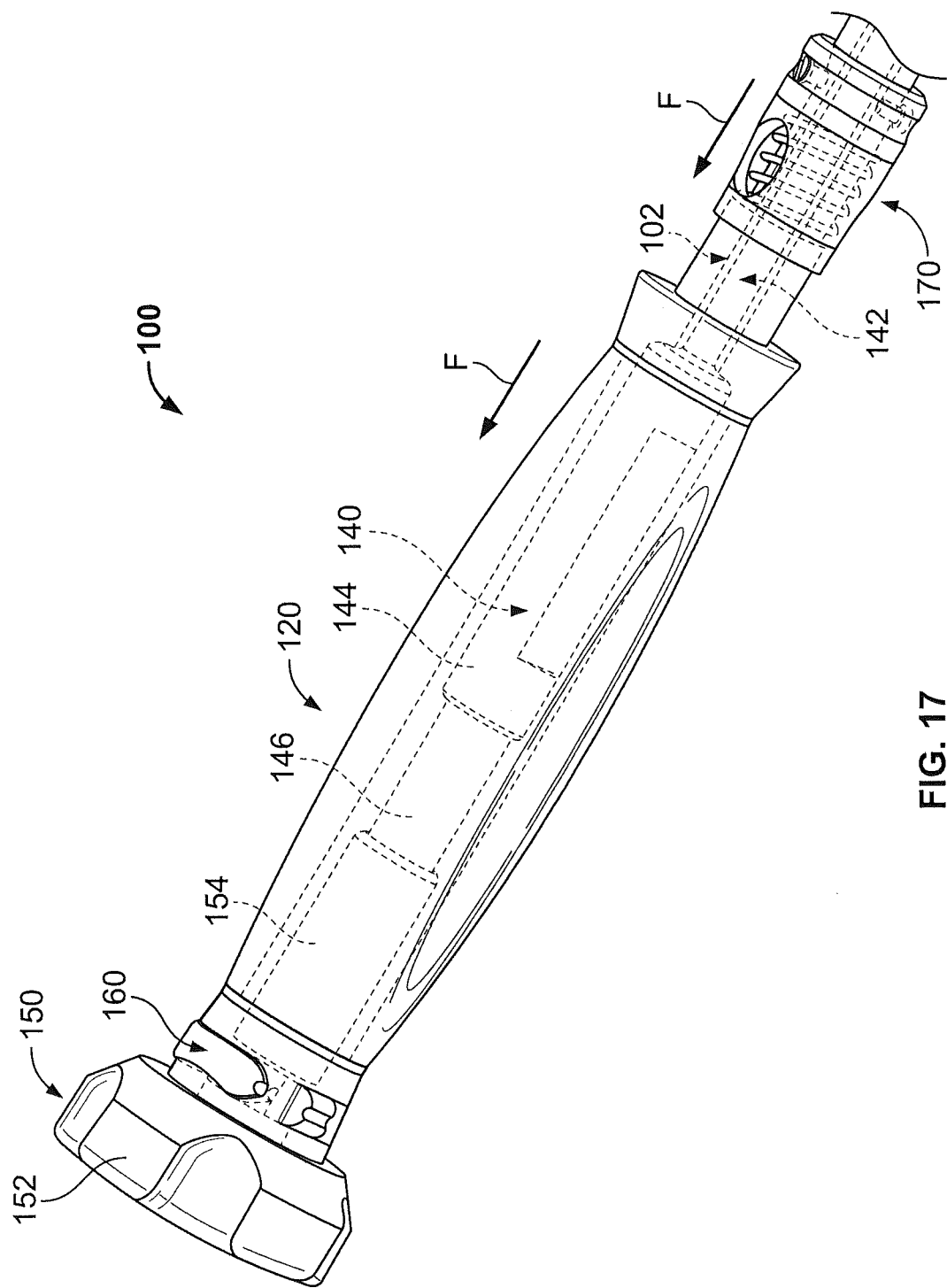
FIG. 17 is a detail of FIG. 16 illustrating a movement of the distal implant fastener reducing the separation distance of FIG. 15 during rotation of the compression member illustrated in FIG. 16 according to the present teachings.

Referring to FIGS. 16 and 17, rotating further the compression member 150 in the direction of arrow C to further tighten the compression member 150 draws the second coupler 140 proximally in the direction of arrow F and reduces or closes the separation distance of the respective female and male tapers 84, 74, thereby securely locking the proximal and distal implants 80, 70 to one another in situ and without removing the assembly tool 100. Rotation of the compression member 150 for fully locking the corresponding tapers 84, 74 of the proximal and distal implants 80, 70 to one another can be facilitated by engaging a wrench or other driver to the attachment feature 151 (shown in FIG. 10) of the compression member.

Summarizing, the assembly tool 100 can be assembled onto the proximal and distal implants 80, 70 sequentially, by first coupling the first coupler 102 to the proximal implant 80 and then assembling the handle member 120 over the first coupler 102 by a quick connection using the locking member 170. The second coupler 140 can be inserted coaxially through the first coupler 102 and through the proximal implant 80 to engage the distal implant 70. Finally, the compression member 150 can be coupled to the handle member 120 and can be engaged to the distal shaft portion 142 of the second coupler 140.

After the proximal and distal implants 80, 70 are fully locked to one another, the assembly tool 100 can be disassembled and removed in the reverse procedure while the tapers 84, 74 of the proximal and distal implants 80, 70 remain securely locked. Specifically, the compression member 150 can be first unscrewed and removed. The second coupler 140 is then unscrewed and removed, followed by the handle member 120 which is released from the first coupler 102 using the locking member 170. The first coupler 102 is then unscrewed and removed.

As discussed above, the assembly tool 100 can be modularly and sequentially assembled onto the proximal and distal implants 80, 70, while holding the respective connecting tapers of the proximal and distal implants 80, 70 at a selected separation distance D. The proximal and distal implants can be impacted into the anatomic site at their final seating depth by impacting the compression member of the assembly tool 100, which is still assembled thereon. Before or during impaction, the implant version can be selected while the assembly tool 100 is fully engaged, by rotating the handle member 120 of the assembly tool 100, without affecting the separation distance D. After the version is selected and the implants are fully seated, the compression member 150 of the assembly tool 100 can be rotated in situ to reduce the separation distance D and lock corresponding tapers 84, 74 of the proximal and distal implants 80, 70. After the tapers 84, 74 of the proximal and distal implants 80, 70 are fully locked and secured, the components of the assembly tool 100 can be disassembled in reverse order of assembly and the assembly tool 100 removed.

It will be appreciated from the above discussion, that the assembly tool 100 can facilitate the procedure of implanting and securing modular components in a sequential manner that guides and assist the medical professional by providing an efficacious in situ assembly and disassembly.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An assembly tool comprising:
a first coupler having a first longitudinal shaft defining a first longitudinal bore, the first coupler engageable to a proximal implant of a modular implant assembly;
a handle member removably couplable with the first coupler, the first coupler received in a longitudinal bore of the handle member;
a second coupler having a second longitudinal shaft passable through the first longitudinal bore of the first coupler, the second longitudinal shaft engageable through the proximal implant to a distal implant of the modular implant, the proximal implant and the distal implant connectable with corresponding tapers;
a slider movably coupled to a proximal portion of the handle member; and
a compression member couplable to the a proximal portion of the second longitudinal shaft, the compression member having an impaction surface and a circumferential groove engageable with the slider by rotating the compression member by a first amount configured to hold the tapers of the proximal and distal implants at a selected separation distance between the tapers while the modular implant assembly is inserted into the anatomic site by impacting the impaction surface, the compression member rotatable by a second amount to reduce the separation distance and engage and lock the tapers of the proximal and distal implants after insertion of the modular implant assembly into the anatomic site.

2. The assembly tool of claim 1, further comprising a locking member having a sleeve with a bore receiving a longitudinal shaft of the handle member and releasably coupling the handle member and the first coupler.

3. The assembly tool of claim 2, wherein the locking member includes a spring held within the sleeve and a ball bearing engageable with a groove of the first coupler through a hole of the longitudinal shaft of the handle member.

4. The assembly tool of claim 1, wherein the slider is spring-biased.

5. The assembly tool of claim 4, wherein the slider produces an audible sound when the slider engages the circumferential groove of the compression member.

6. The assembly tool of claim 1, wherein the handle member includes anti-rotation tabs extending from a distal end of the handle member.

7. The assembly tool of claim 6, wherein the anti-rotation tabs are engageable with corresponding outer slots of the proximal implant and are operable to control a version rotation of the proximal implant by simultaneous rotation of the handle member of the assembly tool as assembled with the proximal and distal implants held thereon.

8. The assembly tool of claim 1, wherein the first coupler is threadably engageable to the proximal implant and the second coupler is threadably engageable to the second implant.

9. The assembly tool of claim 8, wherein the compression member is threadably couplable to the second longitudinal shaft.

10. An assembly tool comprising:
a handle member;
a proximal implant fastener extending from the handle member;
distal implant fastener extending from the handle member; and
a compression member rotatable relative to the handle member, wherein the assembly tool is operable to hold in an assembled configuration of the assembly tool a proximal implant partially engageable with a distal implant during implantation and axial impaction, wherein axial impaction is exerted through an impaction surface on the compression member, and wherein the assembly tool is also operable to securely engage and fully lock corresponding tapers of the proximal and distal implants after impaction by rotating the compression member relative to the handle member to move the distal implant fastener relative to the proximal implant fastener without disassembling the assembly tool, wherein the assembly tool includes in the assembled configuration the proximal implant fastener, the distal implant fastener, the handle member, and the compression member extending along a longitudinal axis.

11. The assembly tool of claim 10, wherein the handle member is a tubular handle member coupling thereon the compression member the proximal implant fastener and the distal implant fastener.

12. The assembly tool of claim 11, wherein the handle member is rotatable to control a selected version of the proximal implant during impaction.

13. The assembly tool of claim 11, wherein the handle member includes a distal portion having an anti-rotation tab engaged with an outer groove of the proximal implant, the anti-rotation tab and the outer groove configured for version control during impaction.

14. The assembly tool of claim 11, further comprising a spring biased locking member releasably coupling the proximal fastener to the handle member.

15. The assembly tool of claim 11, wherein the compression member includes a knob and tubular shaft threadably engageable with a proximal portion of the distal implant fastener through a longitudinal bore of the handle member.

16. The assembly tool of claim 11, further comprising a slider mountable between the compression member and the handle member, the slider spring biased to engage a circumferential groove of the compression member, the slider emitting an audible sound indicative of a relative position of the proximal and distal implants.

17. The assembly tool of claim 10, wherein the compression member includes a circumferential groove engageable with a slider movably coupled to a proximal portion of the handle member by rotating the compression member by a first amount, the first amount configured to hold the tapers of the proximal and distal implants at a selected separation distance between the tapers, the compression member rotatable by a second amount, the second amount configured to reduce the separation distance and engage and fully lock the tapers of the proximal and distal implants.

18. An assembly tool comprising:
- a first coupler having a first longitudinal shaft defining a first longitudinal bore, the first coupler engageable to a proximal implant of a modular implant assembly;
- a handle member removably couplable with the first coupler, the first coupler received in a longitudinal bore of the handle member;
- a second coupler having a second longitudinal shaft passable through the first longitudinal bore of the first coupler, the second longitudinal shaft engageable through the proximal implant to a distal implant of the modular implant, the proximal implant and the distal implant connectable with corresponding tapers;
- a slider movably coupled to a proximal portion of the handle member; and
- a compression member couplable to a proximal portion of the second longitudinal shaft, the compression member having a circumferential groove engageable with the slider by rotating the compression member by a first amount, the first amount configured to hold the tapers of the proximal and distal implants at a selected separation distance between the tapers, the compression member rotatable by a second amount, the second amount to reduce the separation distance and engage and fully lock the tapers of the proximal and distal implants.

19. The assembly of claim 18 further comprising a locking member having a sleeve with a bore receiving a longitudinal shaft of the handle member and releasably coupling the handle member and the first coupler.

20. The assembly tool of claim 19, wherein the locking member includes a spring held within the sleeve and a ball bearing engageable with a groove of the first coupler through a hole of the longitudinal shaft of the handle member.

* * * * *

UNITED STATES PATENT AND TRADEMARK OFFICE
CERTIFICATE OF CORRECTION

| | | |
|---|---|---|
| PATENT NO. | : 8,419,743 B2 | Page 1 of 1 |
| APPLICATION NO. | : 12/718027 | |
| DATED | : April 16, 2013 | |
| INVENTOR(S) | : Aaron P. Smith | |

It is certified that error appears in the above-identified patent and that said Letters Patent is hereby corrected as shown below:

On the Title Page, References Cited, Other Publications, Column 2, line 1, Delete "19sheets." and insert --19 sheets.--.

In the Specification

Column 1, Line 50, After "coupler", insert --,--.

Column 4, Line 32, After "onto", delete "to".

Column 6, Line 31, Delete "FIG. 10)" and insert --FIG. 1C)--.

Signed and Sealed this
Twenty-fifth Day of November, 2014

Michelle K. Lee
*Deputy Director of the United States Patent and Trademark Office*